Sept. 30, 1969 H. HOLTKAMP, SR Plant Pat. 2,922
AFRICAN VIOLET PLANT
Filed Feb. 8, 1968
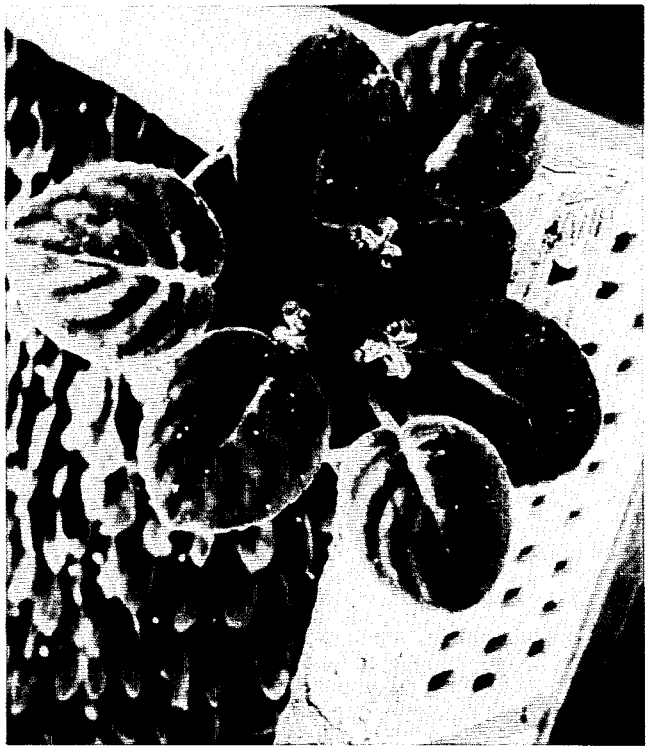
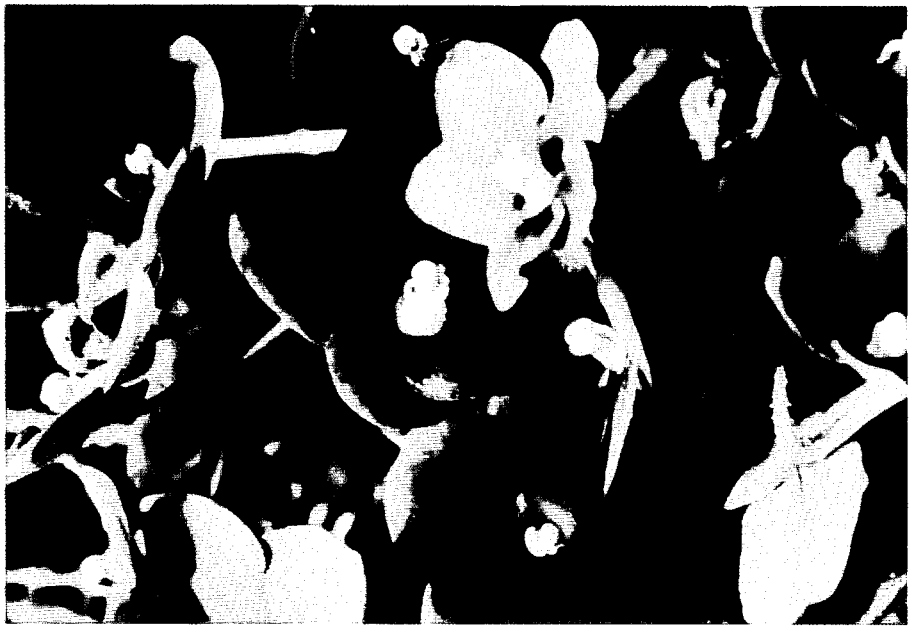
Inventor.
Herman Holtkamp, Sr.
By: Robb & Robb
Attorneys.

United States Patent Office

Plant Pat. 2,922
Patented Sept. 30, 1969

2,922
AFRICAN VIOLET PLANT

Hermann Holtkamp, Sr., 5–7 Werther Strasse,
Isselburg, Rhineland, Germany

Filed Feb. 8, 1968, Ser. No. 704,184
Claims priority, application Germany, May 23, 1967,
H 62,828
Int. Cl. A01h 5/02
U.S. Cl. Plt.—69 1 Claim The present invention relates to a new and distinct variety of African violet plant, botanically known as *Saintpaulia ionantha,* which was originated by me by crossing an unpatented African violet variety, type IV/18 and named "Rhapsody in Blue" with another unpatented African violet variety, type VI/208 and also named "Rhapsody in Blue," the former being the male parent and the latter being the female parent. Both of these parent varieties were previously developed by me as the result of an extensive breeding program.

The primary objective of the new cross of the aforementioned parents was to produce a new and improved African violet variety which bears its flowers singly, without even a trace of an additional wreath of flowers when grown under unfavorable conditions of cultivation, and which retains its blossoms without dropping the same until they have completely faded and dried up. This objective was fully achieved, along with other desirable improved characteristics, as evidenced by the following unique combination of features which distinguish my new variety from its parents, as well as from all other African violet varieties of which I am aware:

(1) An excellent and decorative growth habit, with good sprouting capability;

(2) A habit of bearing its medium to dark green leaves in the form of a bushy but flat rosette;

(3) An upright, solid and dense flower head closed within itself and remaining upright even in a mature state, with the flowers borne singly on strong upright stalks;

(4) An unusual habit of the ovaries, both fructified and unfructified, in pushing through the blossoms so that the receptacle remains in solid cohesion with the ovary and holds the flower until it has completely faded, with consequent avoidance of damage or destruction due to dropped blossoms which tend to cause mildew (botrytis);

(5) A long blooming period; and (6) A distinctive and attractive luminous steel-blue flower color.

The male parent of my new variety is characterized by a bushy as well as a flat habit of growth, has medium and light green foliage and bears large, single, steel-blue blossoms, but drops the blossoms at maturity, while the female parent has very dark foliage and bears its flowers singly in an upright position, and the flowers do not drop off. It also has good disease resistance. The new variety combines the best features of the parent varieties, along with other desirable improvements.

Asexual reproduction of my new variety by leaf cuttings and by division of shoots, as performed by me at Isselburg, Rhineland, Germany, shows that the foregoing characteristics and distinctions come true to form and are established and transmitted through succeeding propagations.

The accompanying drawing shows a typical specimen plant of my African violet variety, as well as typical blooms shown on a somewhat enlarged scale, all as depicted in color as nearly true as it is reasonably possible to make the same in a color illustration of this character.

The following is a detailed description of my new variety, with color terminology in accordance with Hickethier's Color Chart, except where general color terms of ordinary dictionary significance are obvious:

Parentage:

*Male parent.*—"Rhapsody in Blue" type IV/18.

*Female parent.*—"Rhapsody in Blue" type VI/208.

Propagation: Holds its distinguishing characteristics through succeeding propagations by leaf cuttings and by division of shoots.

Plant: From 15 cm. to 20 cm. tall when grown in pots; flower stalks from about 8 cm. to 10 cm. long.

*Leaves.*—Basal; heaped; fleshy; borne in a flat, bushy rosette arrangement of from 15 cm. to 20 cm. in diameter. Shape—elongated obovoid; bluntly notched; length—from 5 cm. to 6 cm; width—about 5 cm. Color: upper side—from medium to dark green; under side—shows red glimmer. Petiole—from oval to round; from about 5 cm. to 7 cm. long.

Flowers:

*Borne.*—In a firm, thick and central flower head, closed within itself above the rosette of leaves and remaining in an upright posture even in their matured state and with the flower stalks pushing toward the middle to form a free bouquet of flowers above the foliage without any need for aligning the same.

*Individual flowers.*—Size—large; from 3.5 cm. to 4.5 cm. in diameter. Color—luminous steel-blue, color No. 099 (Hickethier). Peduncles—multiflorous; up to 8 cm. long; borne in long, shafted cymes, with from 6 to 8 flowers which are quinquepartite, bilaterally symmetrical (zygomorphic). Calyx—lies deep and is also quinquepartite. Corolla tube—very short, with edge spread out in two lips. Stamens—two fructified stamens. Anthers—in large rounded fans which merge together at the bottom and are parallel to each other; color—golden-yellow. Ovary—pilous. Capsule—mostly elongated and incompletely double-fanned. Seed—very small.

Roots: Well developed root zone, with many roots of medium length, while main roots are set with many short sucker and secondary roots. Color—young healthy roots are white, while the roots of older plants have a brownish color.

Disease resistance: Very good resistance to mildew (botrytis) and real blight, as determined by comparison with other African violet varieties grown under the same cultural conditions at Isselburg, Rhineland, Germany.

General observations: Resistant to susceptibility to mutation when grown under conditions unfavorable to cultivation; blooming period is unusually long and therefore fading of the blooms starts very late; growth is very decorative; leaf cuttings shoot forth very well with several corolla so that from 3 to 5 individual plants can be grown by division of shoots from each young plant grown from a single leaf cutting.

I claim:

1. A new and distinct variety of African violet plant, substantially as herein shown and described, characterized particularly as to novelty by the unique combination of an excellent and decorative growth habit, with good sprouting capability, a habit of bearing its medium to dark green leaves in the form of a bushy but flat rosette, an upright, solid and dense flower head closed within itself and remaining upright even in a mature state, an unusual habit of the ovaries, both fructified and unfructified, in pushing through the blossoms so that the receptacle remains in solid cohesion with the ovary and holds the flower until it has completely faded, with consequent avoidance of damage or destruction due to dropped blossoms which tend to cause mildew (botrytis), a long blooming period, and a distinctive and attractive luminous steel-blue flower color.

No references cited.

ROBERT E. BAGWELL, Primary Examiner